(12) United States Patent
Levine et al.

(10) Patent No.: US 7,318,814 B2
(45) Date of Patent: *Jan. 15, 2008

(54) MEDICAL SUCTION VALVE

(75) Inventors: Andy H. Levine, Newton Center, MA (US); Eric E. May, Norfolk, MA (US); Anthony R. Tremaglio, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/216,974

(22) Filed: Aug. 12, 2002

(65) Prior Publication Data

US 2002/0188175 A1 Dec. 12, 2002

Related U.S. Application Data

(60) Continuation of application No. 09/649,129, filed on Aug. 28, 2000, now Pat. No. 6,447,473, which is a division of application No. 09/302,671, filed on Apr. 30, 1999, now Pat. No. 6,254,061.

(51) Int. Cl.
*A61M 1/00* (2006.01)

(52) U.S. Cl. ...................................................... 604/33

(58) Field of Classification Search ............ 604/33–36, 604/30, 93.01, 95.04, 95.05, 164.01, 167.01, 604/167.02, 167.03, 264, 523, 38, 27, 95.01, 604/95.02, 164.11, 164.13, 167.05, 533, 534, 604/535, 537, 284, 167.04; 137/109, 111, 137/142, 246, 246.11, 246.21, 246.22, 247.11, 137/247.13, 247.27, 247.29, 494, 495, 625, 137/625.25, 629.26, 625.67, 625.68, 625.69

See application file for complete search history.

(56) References Cited

U.S. PATENT DOCUMENTS

| 1,527,872 A | | 2/1925 | Herrick |
| 3,469,582 A | | 9/1969 | Jackson |
| 3,625,221 A | | 12/1971 | Corbett |
| 3,645,497 A | | 2/1972 | Nyboer |
| 3,918,680 A | * | 11/1975 | Stevens, Jr. ................. 251/287 |
| 3,993,099 A | | 11/1976 | Nightingale |
| 4,031,918 A | * | 6/1977 | Cagle .................... 137/625.23 |
| 4,210,178 A | * | 7/1980 | Morse et al. ............ 137/625.5 |
| 4,248,214 A | * | 2/1981 | Hannah et al. ............. 604/523 |
| 4,356,823 A | | 11/1982 | Jackson |
| 4,414,999 A | * | 11/1983 | Basta ......................... 137/240 |
| 4,517,962 A | | 5/1985 | Heckele |
| 4,673,393 A | * | 6/1987 | Suzuki et al. .......... 604/167.04 |
| 4,736,732 A | | 4/1988 | Shimonaka et al. |
| 4,741,326 A | | 5/1988 | Sidall et al. |
| 4,886,507 A | * | 12/1989 | Patton et al. ............... 604/284 |
| 5,104,387 A | * | 4/1992 | Pokorney et al. ........... 604/248 |
| 5,135,026 A | * | 8/1992 | Manska ...................... 137/555 |
| 5,176,698 A | * | 1/1993 | Burns et al. ................ 606/192 |
| 5,188,591 A | | 2/1993 | Dorsey, III |
| 5,224,929 A | | 7/1993 | Remiszewski |
| 5,247,966 A | * | 9/1993 | Stevens et al. ......... 137/625.69 |
| 5,295,956 A | | 3/1994 | Bales et al. |
| 5,391,145 A | | 2/1995 | Dorsey, III |
| 5,447,494 A | | 9/1995 | Dorsey, III |
| 5,460,614 A | * | 10/1995 | Castaneda .............. 604/164.13 |
| 5,505,710 A | | 4/1996 | Dorsey, III |
| 5,573,504 A | | 11/1996 | Dorsey, III |
| 5,584,803 A | * | 12/1996 | Stevens et al. ............. 604/6.16 |
| 5,722,949 A | | 3/1998 | Sanese |
| 5,766,211 A | | 6/1998 | Wood et al. |
| 5,840,015 A | | 11/1998 | Ogino |
| 5,993,410 A | * | 11/1999 | Vincent et al. ................ 604/27 |
| 6,170,493 B1 | * | 1/2001 | Sivacoe ......................... 134/8 |
| 6,254,061 B1 | * | 7/2001 | Levine et al. ................ 251/325 |
| 6,258,072 B1 | * | 7/2001 | Weinberger .................. 604/284 |
| 6,447,473 B1 | * | 9/2002 | Levine et al. ................. 604/33 |
| 6,482,189 B2 | * | 11/2002 | Dopper et al. ............... 604/284 |

FOREIGN PATENT DOCUMENTS

| DE | 3629857 | 3/1987 |
| DE | 19610312 | 9/1996 |
| FR | 1331269 | 5/1963 |
| FR | 1397730 | 3/1965 |
| WO | WO 1397730 | 3/1965 |

(Continued)

OTHER PUBLICATIONS

American Urological Association, Inc., Ureteral Stones Pamphlet, pp. 1-5, 7-8 (1997).

(Continued)

*Primary Examiner*—Ann Yen Lam

(57) ABSTRACT

A valve assembly includes a housing defining an aperture, a passageway, and a branch passage. The branch passage extends from the aperture and intersects and communicates with the passageway. The branch passage is disposed at an angle greater than 90 degrees with respect to the passageway. A piston is disposed at least partially within the branch passage and is movable from a first position to a second position. The piston allows communication between the passageway and the aperture when the piston is in the first position, and the piston blocks communication between the passageway and the aperture when the piston is in the second position. An angled seal may be positioned around the piston.

24 Claims, 10 Drawing Sheets

FOREIGN PATENT DOCUMENTS

| | | |
|---|---|---|
| WO | WO 98/46299 | 10/1998 |
| WO | WO 98/46300 | 10/1998 |
| WO | WO 00/66194 | 11/2000 |

OTHER PUBLICATIONS

Boston Scientific/Microvasive Education Center, "Percutaneous Nephrolithomoty," pp. 1-10 (1995).

Boston Scientific/Microvasive Catalog, "Swiss Lithoclast Pneumatic Lithotriptor System" (1998).

International Search Report for International Patent Application Serial No. PCT/US00/11476, dated Nov. 3, 2000, 7 pgs.

Partial International Search Report for International Patent Application Serial No. PCT/US00/11476, dated Aug. 28, 2000, 2 pgs.

Smith, "Percutaneous Removal of Kidney Stones," Urologic Surgery, pp. 116-131, date unknown.

Smith, "Percutaneous Removal of Kidney Stones," Urologic Surgery, pp. 116-131, date not available.

* cited by examiner

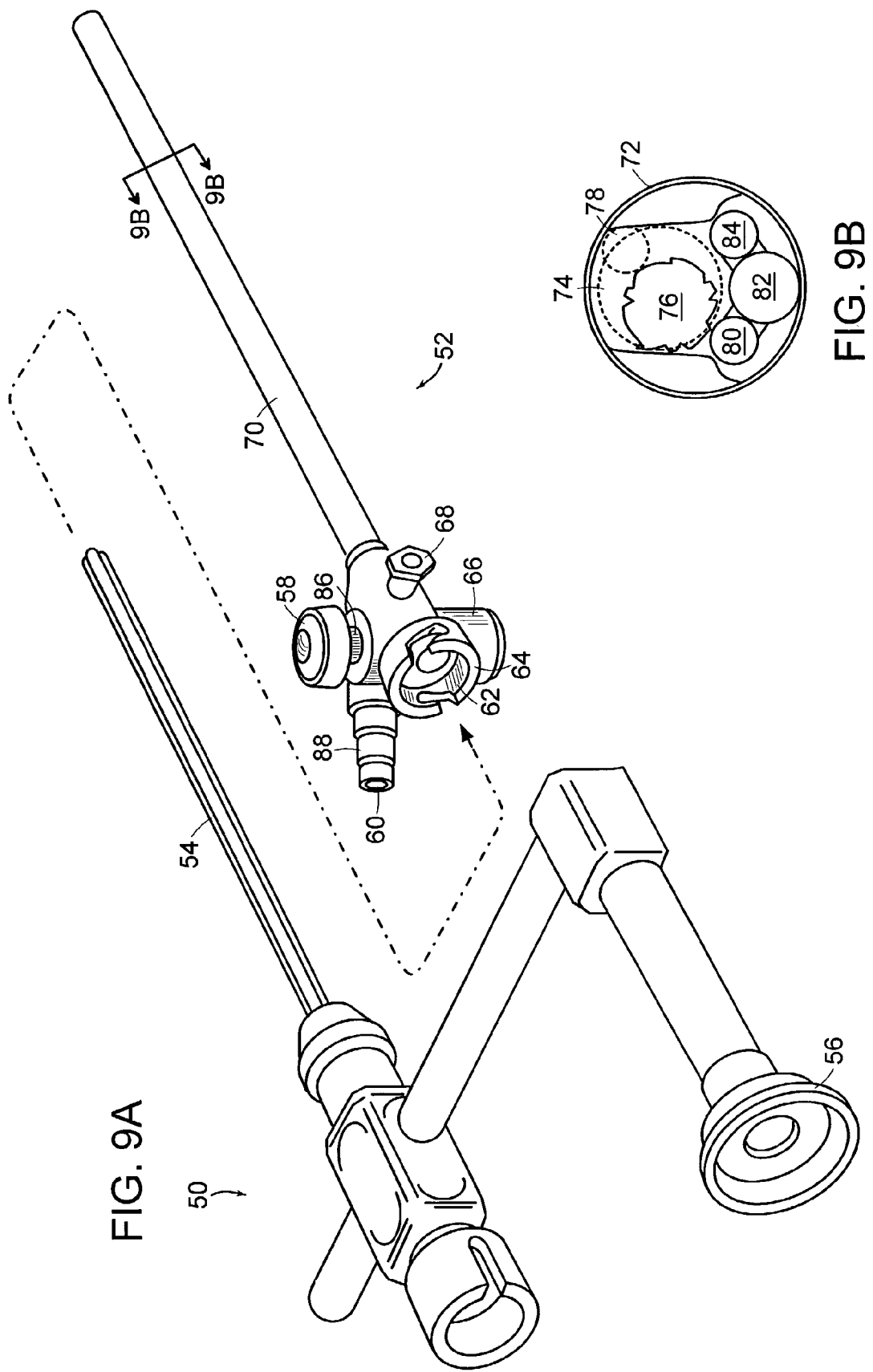

MEDICAL SUCTION VALVE

CROSS-REFERENCE TO RELATED APPLICATIONS

The present application is a continuation of U.S. Ser. No. 09/649,129, filed on Aug. 28, 2000, now U.S. Pat. No. 6,447,473 which is a division of U.S. Ser. No. 09/302,671, filed on Apr. 30, 1999, now U.S. Pat. No. 6,254,061, the entire disclosures of both of which are incorporated herein by reference.

TECHNICAL FIELD

The invention relates generally to devices that provide suction through a sheath and a valve. More particularly, the invention relates to medical devices that provide suction through a sheath and a valve in conjunction with an endoscopic medical device.

BACKGROUND INFORMATION

Many medical procedures utilize an endoscopic medical device to visualize tissue contained within a patient during the medical procedure. Typically, medical procedures of this type are minimally invasive, and the ability to remove materials in the operating area with suction and/or irrigation is desirable. For example, nephroscopic or uroscopic procedures can use suction and irrigation.

Current designs of devices for providing suction during an endoscopic procedure have various problems. For example, some designs require the debris that is removed from the site of the operation to travel through valves, and related conduits, that contain sharp angles (e.g., 90 degree angles). Also, some designs require valves to be manufactured with close tolerances between parts, increasing the cost of the valve and the overall medical device. Known devices have other problems as well.

SUMMARY OF THE INVENTION

The present invention provides a device capable of controlled suction. Devices according to the invention minimize the chances that material removed from a patient will clog a device. Additionally, valves of the invention utilize seals which can be constructed with looser tolerances between components than current designs. Thus, devices and valves of the invention perform substantially better than current devices and are more easily manufactured than current devices.

In one aspect of the invention, a valve assembly comprises a housing defining an aperture, a passageway, and a branch passage. The branch passage extends from the aperture and intersects and communicates with the passageway. The branch passage is disposed at an angle greater than 90 degrees with respect to the passageway. A piston is disposed at least partially within the branch passage and is movable from a first position to a second position. The piston allows communication between the passageway and the aperture when the piston is in the first position, and the piston blocks communication between the passageway and the aperture when the piston is in the second position.

In certain embodiments, the valve assembly can have any of the following features. The piston can be biased toward the second position. The housing can further define a second aperture and/or a third aperture. A sheath can extend from the second aperture. A connector can be associated with or formed from the third aperture for coupling to an endoscopic medical device. The housing also can further define at least one port in communication with the passageway. Additionally, an angled seal may be positioned around the piston. This angled seal can be an O-ring.

In another aspect of the invention, a sheath assembly for use with an endoscopic medical device comprises a valve assembly and a sheath. The valve assembly comprises a housing defining a passageway and a branch passage. The branch passage intersects and communicates with the passageway and is disposed at an angle greater than 90 degrees with respect to the passageway. The sheath extends from the passageway and is capable of passing over at least a portion of the endoscopic medical device.

In certain embodiments, the sheath assembly can have any of the features described above and any of the following features. The sheath can be translucent, transparent, and/or flexible. The sheath can define an irrigation channel. An outer wall of the sheath can define a channel for receiving at least a portion of the endoscopic medical device. The outer wall can be capable of conducting light. The sheath assembly can further comprise a pull wire that, when actuated, produces a curvature of the sheath. The rigid or flexible sheath can also include an internal divider defining at least two channels and/or two lumens within the sheath. The internal divider can be integral with the outer wall. The pull wire can extend through at least one of the channels. At least one of the channels can accept the endoscopic medical device. Other channels can optionally accept a different medical device. The valve assembly can be releasably attachable to the endoscopic medical device.

In another aspect, a valve assembly comprises a housing, a piston disposed at least partially within the housing, and an angled seal around the piston. In certain embodiments, the valve assembly can have any of the features described above.

BRIEF DESCRIPTION OF THE DRAWINGS

In the drawings, like reference characters generally refer to the same parts throughout the different views. Also, the drawings are not necessarily to scale, emphasis instead generally being placed upon illustrating principles of the invention.

FIG. 9A shows another embodiment of a sheath assembly according to the invention, in association with an endoscopic medical device.

FIG. 9B is a view in cross-section of the sheath portion of the assembly of FIG. 9A, taken along line 9B-9B of FIG. 9A.

DESCRIPTION

Figure 1:
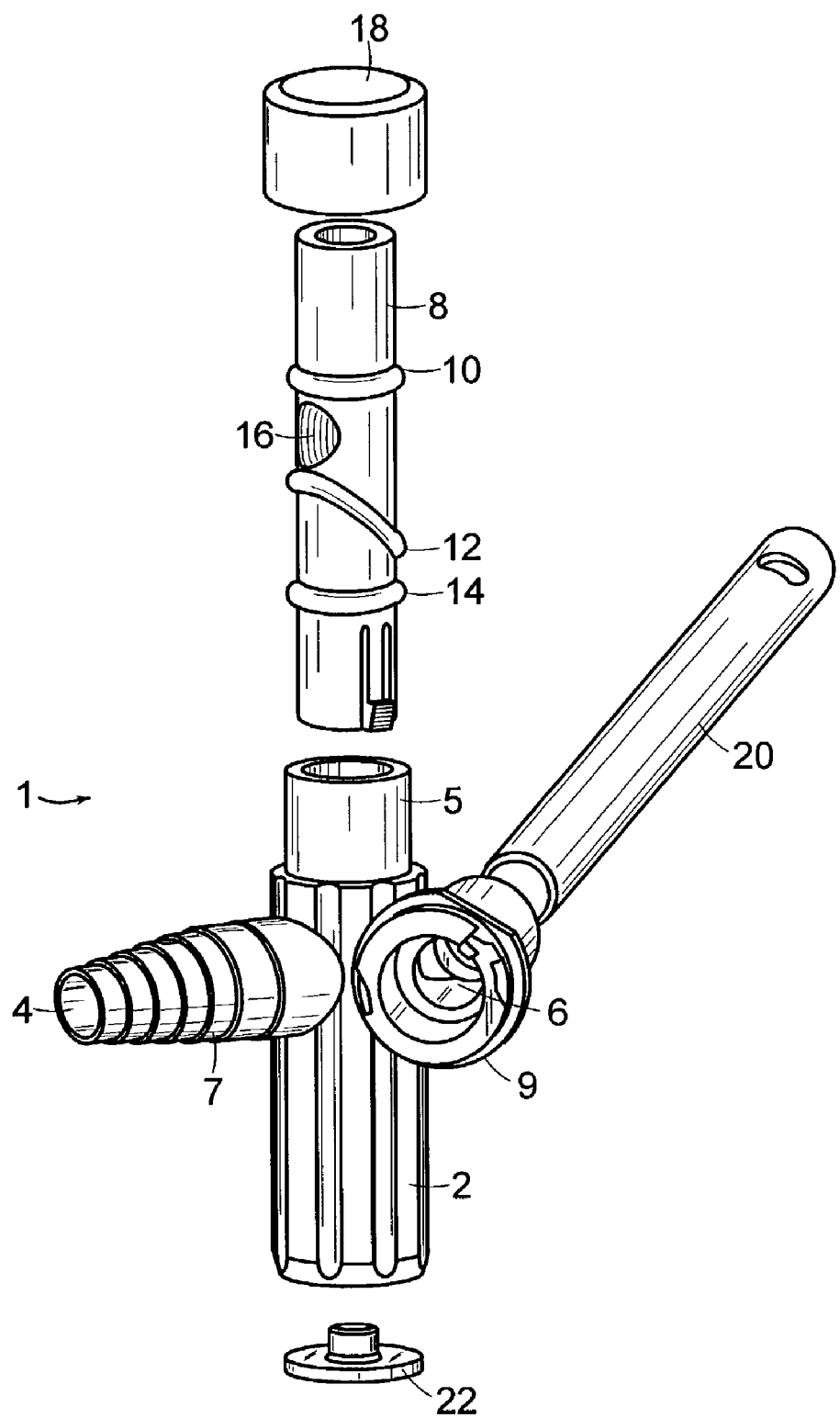
FIG. 1 is an exploded view of one embodiment of a sheath assembly according to invention.

The present invention provides a device capable of controlled suction. Designs of the invention minimize clogging and allow for relatively loose tolerances between components. Additionally, devices according to the invention provide a larger area through which materials are suctioned and can be flexible or selectively flexible. The invention has beneficial application in many different medical procedures. Generally, such procedures are those that are minimally invasive and utilize a sheath to hold open tissue during the operation. Also, the invention is particularly useful in conjunction with an endoscopic device.

Percutaneous nephrolithotomy ("PCNL") and ureteroscopy are two examples of medical procedures utilizing endoscopic technique. The medical professional visualizes the inside of a patient's body while performing medical manipulations through a "working" sheath that exits a patient's body at a particular point. Materials, such as a stone, are removed from a patient with, for example, a suction device.

During the PCNL procedure, a medical professional makes a small incision in a patient's skin on the lower back. Although many variations of PCNL procedures exist, most variations share several common steps. First, a guidewire is inserted through the incision and into the kidney. Dilators are advanced over the guidewire and actuated, pushing apart the tissue surrounding the dilator. A "working" sheath is advanced over the dilator and inserted into the patient's kidney to hold open a passageway through the tissue surrounding the guidewire. Next, a nephroscope is inserted through the sheath. The medical professional uses the nephroscope to visualize tissue and other material at the opening of the sheath inside the patient. Then, with current devices, a lithotriptor and/or a grasping device and/or a small suction device is inserted through the sheath, next to or through the nephroscope. The lithotriptor fragments a stone; the grasping device captures a stone or fragments of a stone which is then removed from the kidney; and the suction device uses suction to remove a whole stone or fragments of a stone from the kidney.

Similarly, during ureteroscopy, a medical professional inserts a ureteroscope through the urethra and bladder, into the ureter. The ureteroscope is used to visualize tissue within the patient's body. Also, the ureteroscope can be used in conjunction with a "working" sheath through which different tools can be advanced. For example a lithotriptor and/or a grasping device and/or a small suction device can be inserted through the sheath, next to or through the ureteroscope, to remove a stone from the ureter similar to the manner described above.

Designs of the invention, typically include a sheath attached to a valve. Materials, such as a stone or fragments from a stone, are suctioned through the "working" sheath and enter the valve. Unlike current devices, when materials move through the various passageways within the valve, they do not abruptly change their direction of travel. Abrupt changes in the direction of travel tend to clog current devices as the material becomes impinged against the walls of passageways where the changes occur and/or become stuck against protrusions in the passageways associated with the changes. Thus, the chances of devices of the invention becoming clogged with material removed from a patient are minimized. Additionally, current devices, typically, have components that are machined to fit together tightly and are constructed from materials, such as metals, that allow for this fine machining. In contrast, valves of the invention, utilizing seals, can be constructed with looser tolerances and less expensive materials, such as, but without limitation, thermopolymers. Thus, by avoiding a tendency to clog and by using seals, the device performs substantially better and is more easily manufactured than current devices.

Additionally, designs of the invention allow a larger area of the sheath to be used for material removal. Current suction devices are inserted through the "working" sheath in order to have access to and to remove material, limiting their cross-sectional area to one relatively smaller than that of the "working" sheath. The functional sheaths of the invention can be used as a "working" sheath, holding open a tissue passageway during an endoscopic procedure such as PCNL. Thus, the entire cross-sectional area of the sheath of devices of the invention, less any portion used by other medical devices inserted through the sheath, is available to remove materials. Consequently, larger materials may be removed with devices of the invention than with current devices. Additionally, using the sheath according to the invention as the "working" sheath allows the medical professional to use a smaller sheath (because more of it is available for suction), if desired. A smaller sheath decreases the size of the incision and the tissue passageway in the patient, decreasing patient pain and/or bleeding. Also, stones and fragments of stones can more easily be prevented from migrating away from the operation area because a medical professional can quickly activate suction devices of the invention to remove materials. Furthermore, because the devices currently used to provide suction are rigid and are inserted through the sheath, the sheath is not bendable. However, designs of the invention, which do not require a rigid suction device because suction is provided directly through the sheath itself, allow some embodiments to have flexible and deflectable sheaths.

Figure 2:
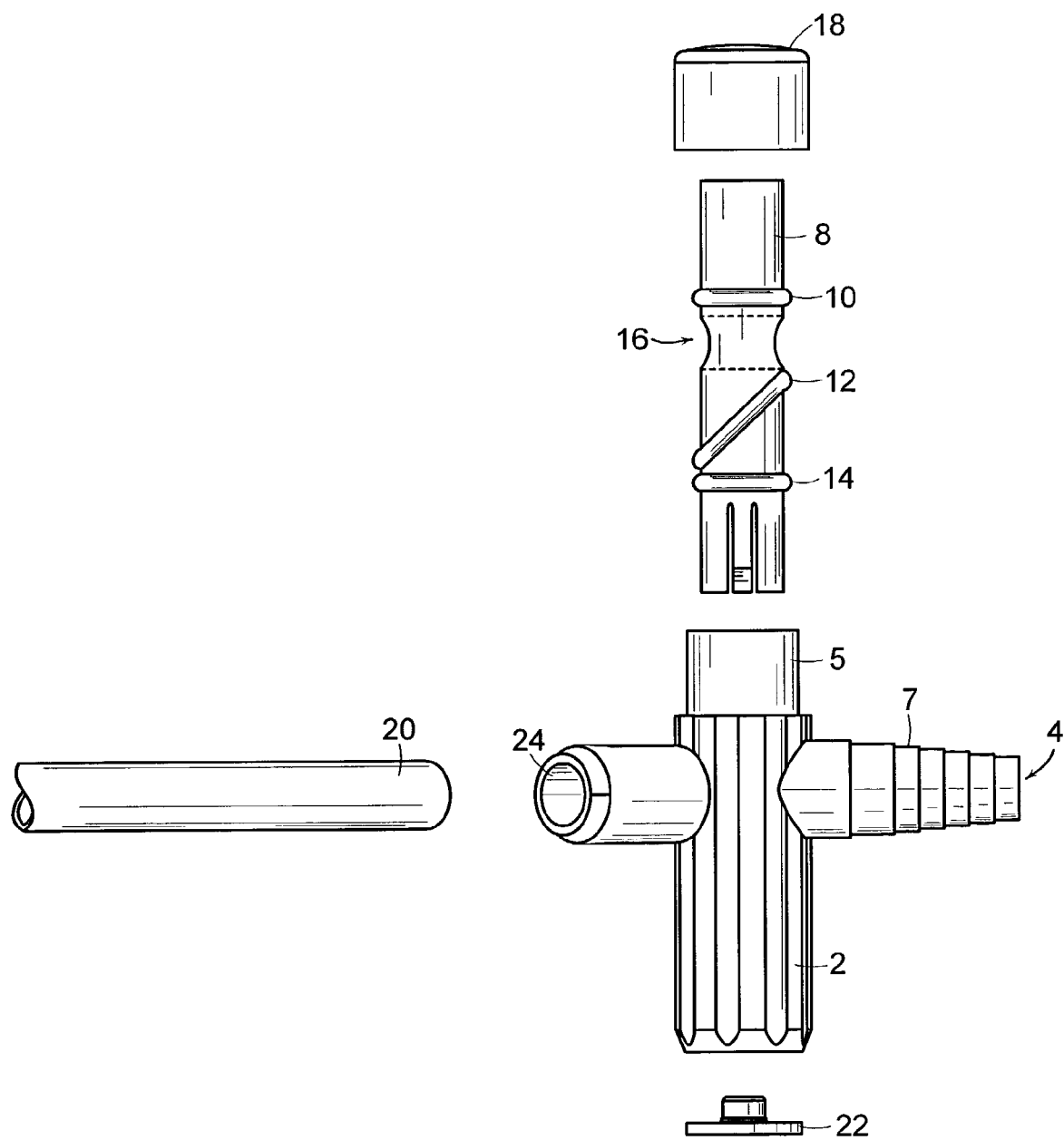
FIG. 2 shows the exploded assembly of FIG. 1 rotated about 180 degrees from the position depicted in FIG. 1.
Figure 3:
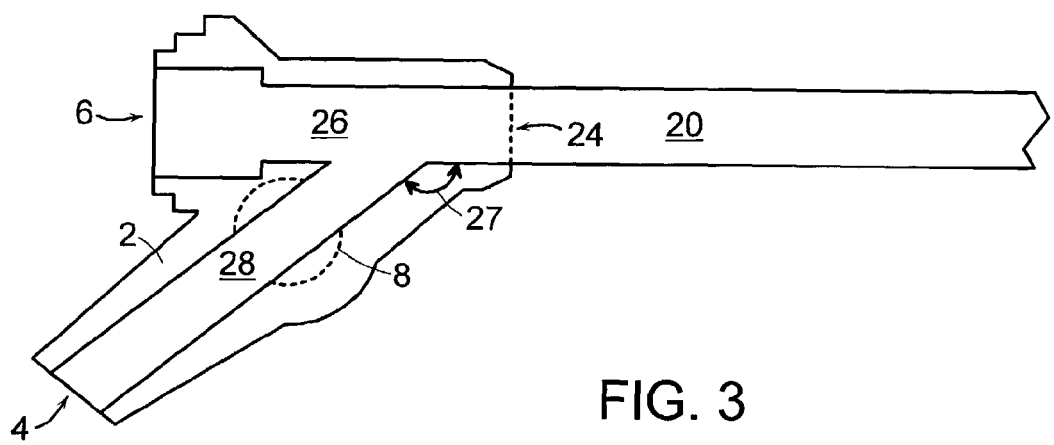
FIG. 3 is a cross-sectional view through and along the nozzle and the sheath of the assembly of FIG. 1, when viewed from the bottom of the assembly of FIG. 1.
Figure 4A:
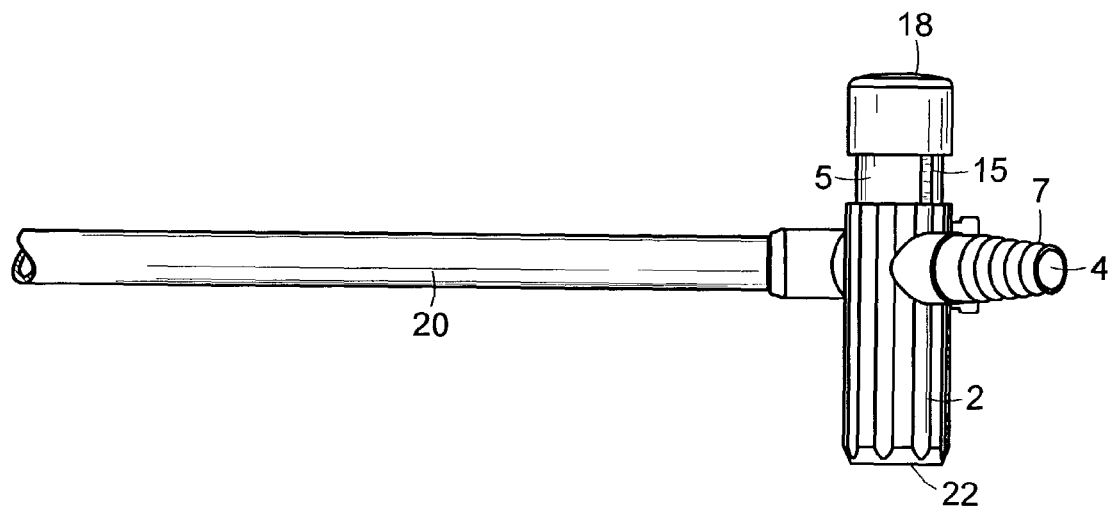
FIG. 4A shows the assembly of FIG. 1 in an assembled form.
Figure 4B:
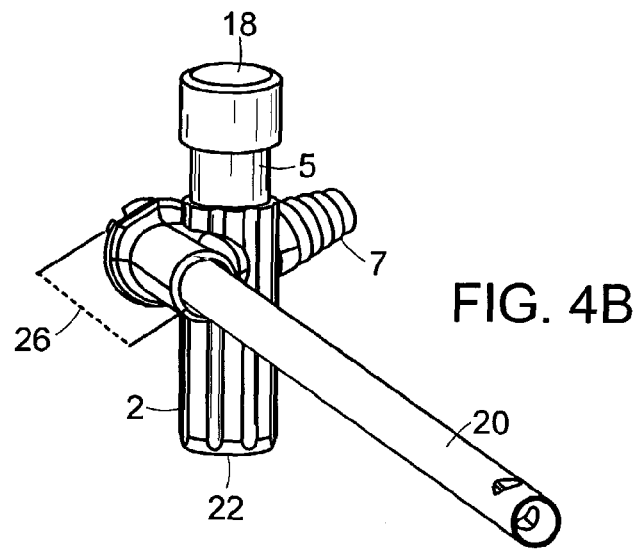
FIG. 4B shows the assembly of FIG. 4A rotated about 90 degrees from the position depicted in FIG. 4A.
Figure 5:
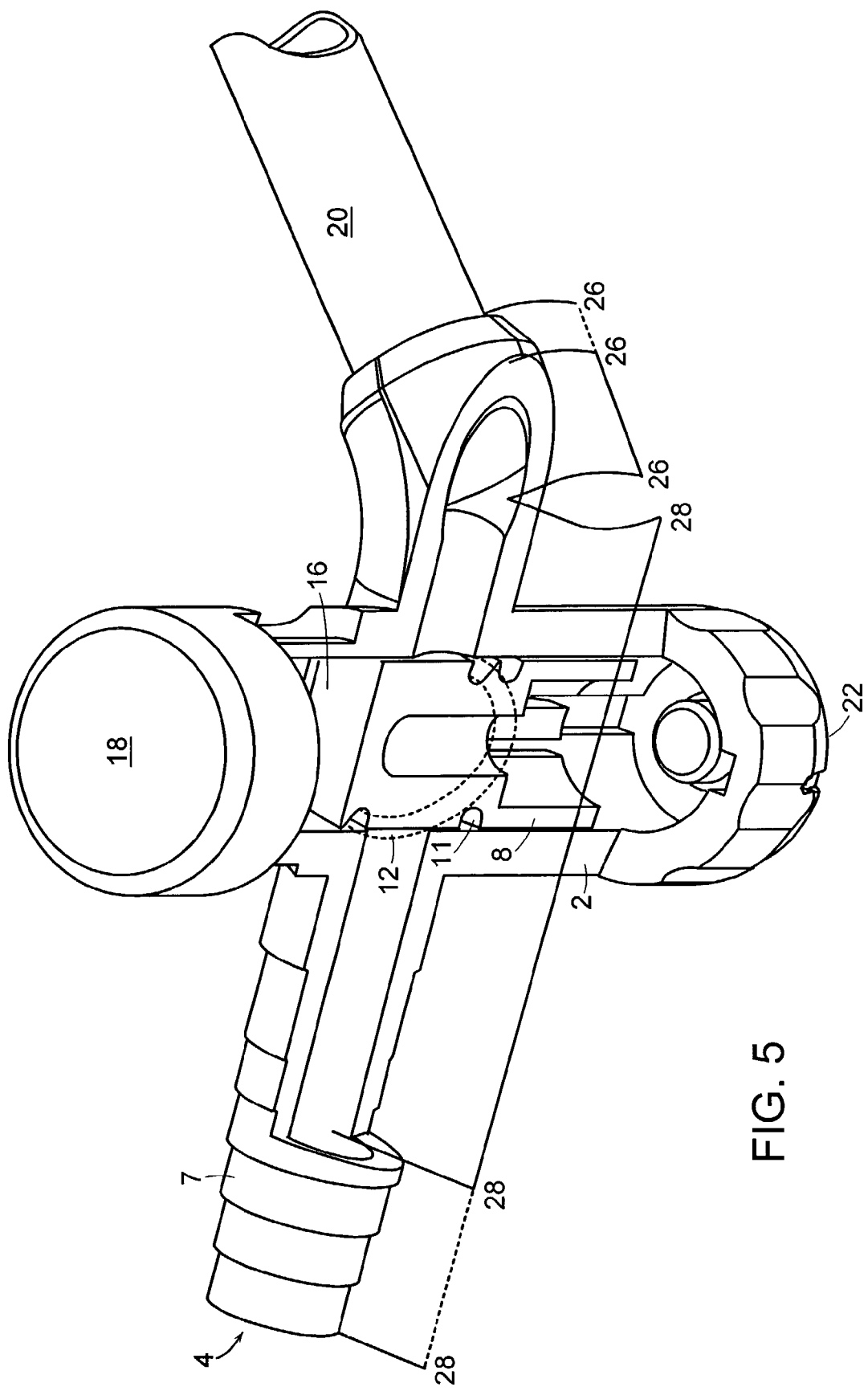
FIG. 5 is a perspective view in partial cross-section of the assembly of FIGS. 4A and 4B.

Referring to FIGS. 1,2,3,4A,4B, and 5, a sheath assembly 1 includes a housing 2, a piston 8, and a sheath 20. The piston 8 fits within the housing 2. A cap 18, suitable for a medical professional's digit to operate the piston 8 is included. A protrusion 15 on a collar 5 that extends from (and can be a part of ) the housing 2 engages with the cap 18 to properly align the piston 8 within the housing 2 (FIG. 4A). A bottom cap 22 seals the housing 2 at its bottom. The sheath 20 attaches to the housing at an opening 24 in the housing 2 (FIG. 2). The opening 24 communicates with an opening 6 at the opposite end of a passageway 26 contained within the housing 2 (FIG. 3). This passageway 26, typically, is an entry point for medical instruments such as, but not limited to, a lithotriptor or an endoscopic medical viewing device. Disposed about the opening 6 is a connector 9 which allows for mounting the housing 2 to an endoscopic medical device. A third opening 4 is an exit from a branch passageway 28 contained within a nozzle 7 and extending until it intersects with the other passageway 26 (FIG. 3). In accordance with the invention, the intersection of the passageway 26 and the branch passageway 28 occurs at an angle 27 greater than 90 degrees.

In typical embodiments, a device that creates suction (or tubing that is attached to such a device) is attached to the nozzle 7 and communicates with the valve assembly (which generally includes the housing 2 and the piston 8 that fits at least partially therewithin) and the sheath 20. This suction device (e.g., but without limitation, a vacuum) creates a suction force with a vector direction from the distal tip of the sheath 20 to the opening 4 in the nozzle 7. Thus, suction normally moves materials to be removed from the body through the sheath, a portion of the passageway 26, the branch passageway 28, and out of the opening 4. This removal path has no abrupt changes in direction. Materials flow smoothly through the sheath 20 and through a portion of the passageway 26 and the branch passageway 28. Any tendency to clog in the passageway 26 or the branch passageway 28 is reduced because of the non-abrupt, greater than 90° angle 27 configuration of the branch passageway 28 with respect to the passageway 26.

Seals 10, 12, 14 contact both the piston 8 and the inside of a space within the housing 2 that is complementary to the piston 8, and they provide a reliable seal. Each of these seals 10, 12, 14 are shown as an O-ring. The seals, 10, 12, 14 fit within retention grooves 11 (only one groove is labeled, for clarity). One of the seals 12 is disposed about the piston at an angle relative to a plane that is perpendicular to and cuts through the piston 8. As one of ordinary skill will appreciate, any seal that reliably prevents leaking between the piston and the inside of the housing is useful in the present invention. Between this angled seal 12 and the upper most seal 10 lies an opening 16 in the piston 8.

The nature of the O-rings, particularly the angled O-ring, serves to compensate for any imprecision in manufacturing the housing 2 and/or the piston 8. The O-ring is both compliant and resilient. For example, but without limitation, the O-ring can be made from synthetic and/or natural rubber, silicone, buna-n, butyl, or any other compliant and resilient materials. Thus, the O-ring can conform to irregularities in the surfaces that it contacts. Moreover, the dimensions of the space within the housing 2 and the piston 8 do not need to be manufactured to precise tolerances. In current devices, metals are utilized to allow a close fit between the piston and the space surrounding the valve. However, in the present invention, a relatively looser fit is possible between the piston 8 and the space surrounding the housing 2. Thus, materials such as thermopolymers (for example, but without limitation, acrylonitrile butadiene styrene ("ABS") or polycarbonate), typically less expensive than metals, can be used in manufacturing processes, such as molding, to form the housing 2 and the piston 8. These manufacturing processes, also, are typically less expensive than those used with high tolerance metal components. Moreover, these less expensive materials, facilitated by the O-rings, allow devices according to the invention to be disposable. As one of ordinary skill will appreciate, any seal that allows designs of the invention to have relatively loose tolerances between components is useful.

Figure 6:
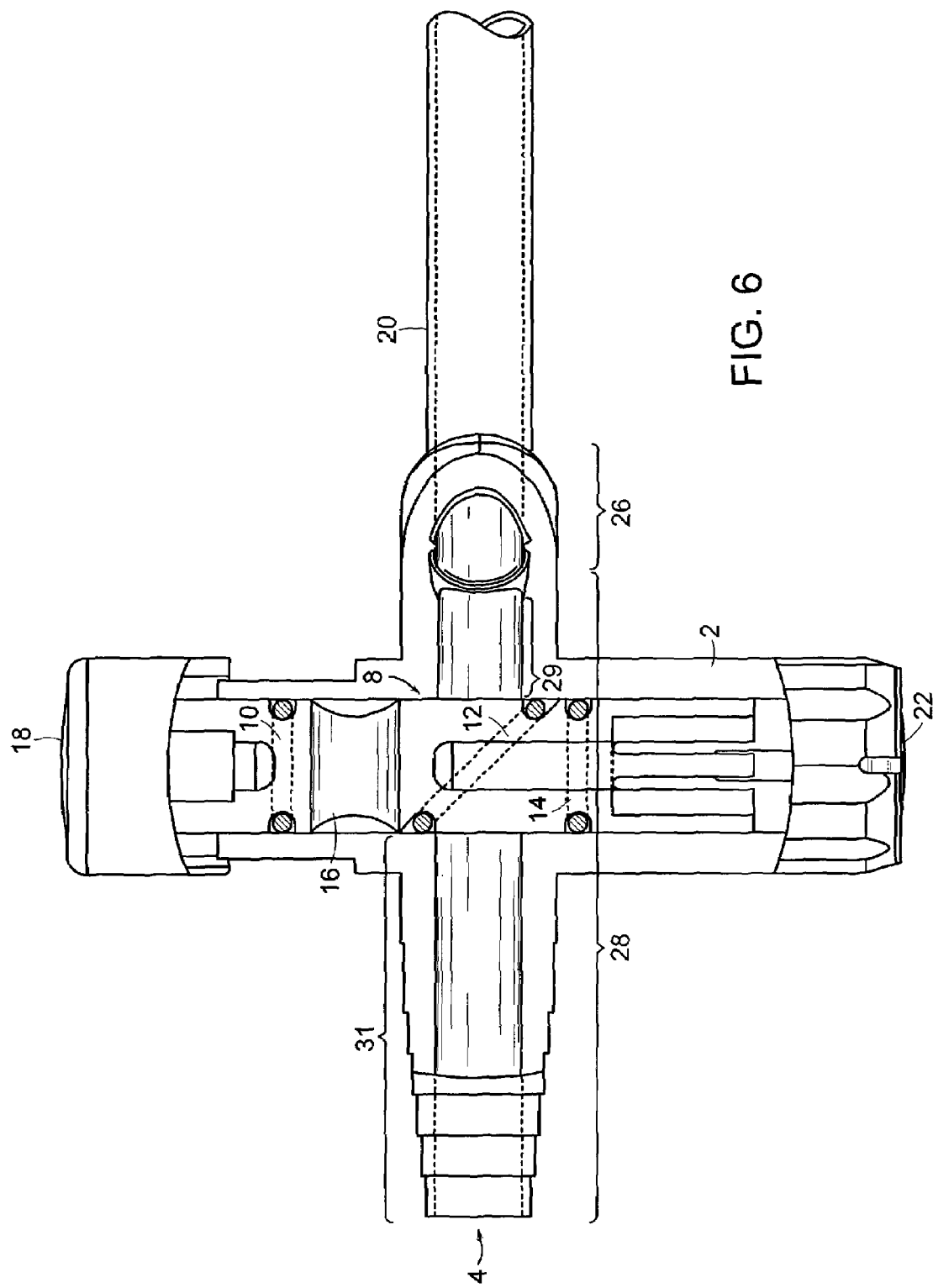
FIG. 6 is another view in partial cross-section of the assembly of FIG. 5 with the piston in an "off" position, as it is in FIG. 5.
Figure 7:
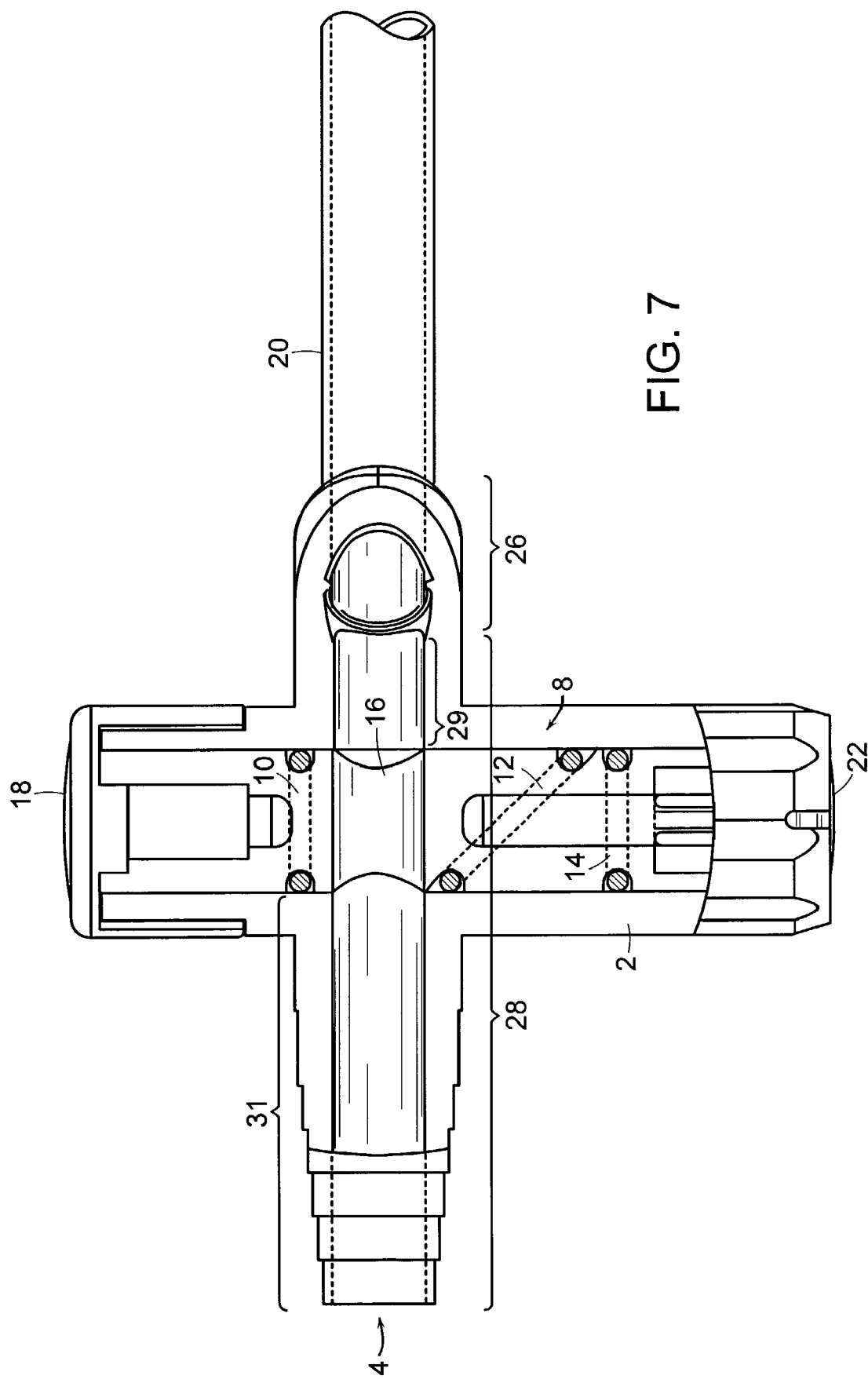
FIG. 7 is a partial cross-sectional view similar to that shown in FIG. 6 but with the piston in an "on" position.
Figure 8:
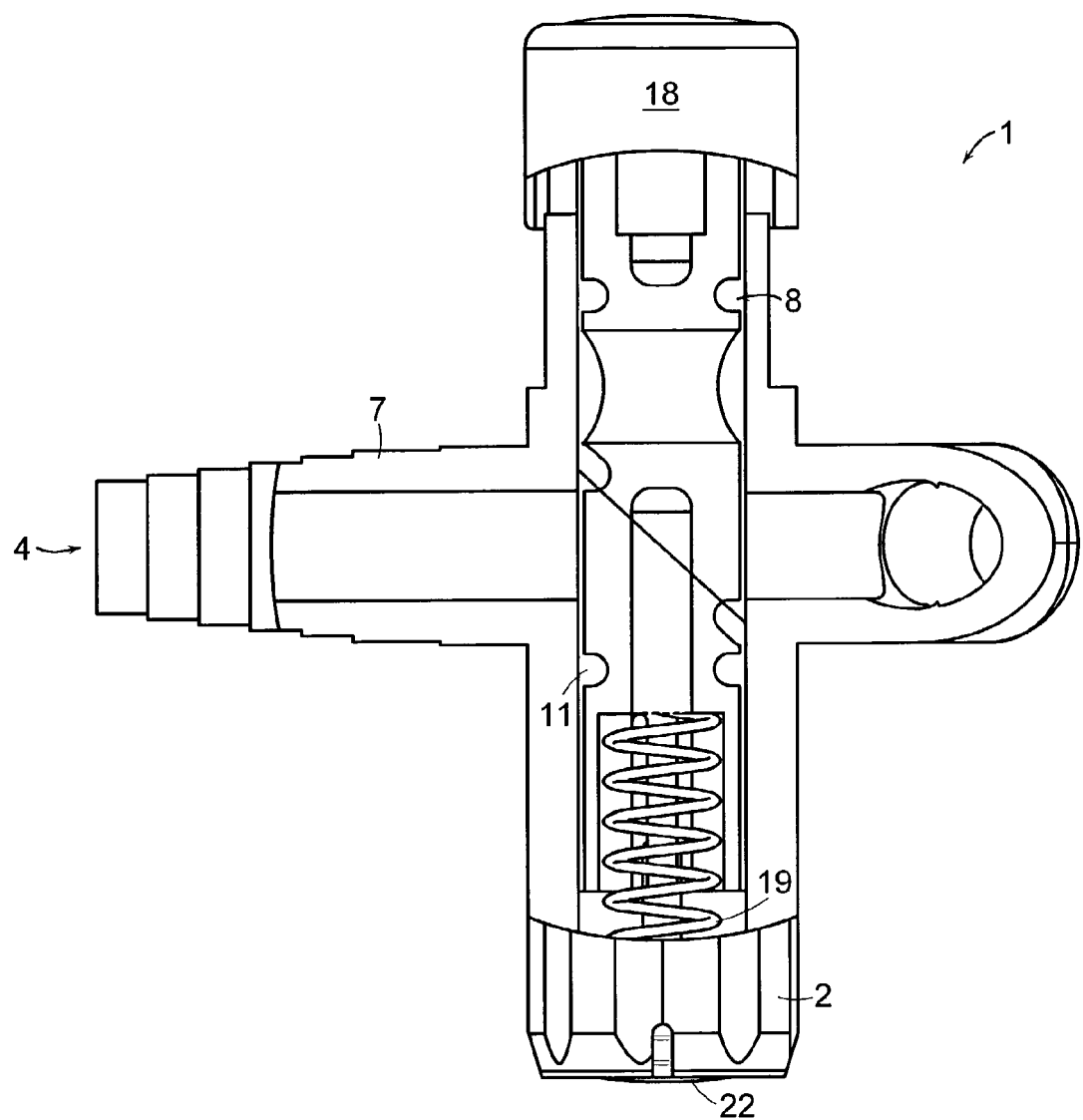
FIG. 8 is a partial cross-sectional view similar to that of FIG. 6 but with the seals and the sheath missing and with a valve biasing mechanism present.

Now referring to FIGS. 6, 7, and 8, the opening 16 allows materials to move through the branch passageway 28 which branches from the passageway 26 and which is interrupted by the piston 8. When the piston 8 is in the "off" position as shown in FIG. 6, the passageway 28 is blocked by a portion of the piston 8. Typically, the piston 8 is biased towards the "off" position by, for example, but without limitation, a spring 19, shown in FIG. 8. Other types of valve biasing mechanisms could be used instead of the spring 19. The seal 12, due to the angle at which it is disposed about the piston 8, in conjunction with seals 10, 14 prevents communication between two portions 29, 31 of the branch passageway 28 through the space between the housing 2 and the piston 8 (i.e., the two portions 29, 31 of branch passageway 28 are sealed from each other). Thus, suction is not available beyond the piston 8, to, for example, the sheath 20, and materials are unable to move within the sheath 20 or the passageway 26. The sheath 20 extends beyond what is pictured in FIG. 6.

When the piston 8 is in the "on" position as shown in FIG. 7, an unobstructed pathway is created from the distal tip of sheath 20, through the passageway 26, through the first portion 29 of the branch passageway 28, through the opening 16 in the piston 8, through the second portion 31 of the branch passageway 28, to the opening 4. The seal 12, due to the angle at which it is disposed about the piston 8, in conjunction with seals 10, 14 prevents leakage of suction force or of suctioned materials between the housing 2 and the piston 8. The opening 16 in the piston 8 provides a smooth transition between the two portions 29, 31 of the branch passageway 28. Materials travel in a straight line through the branch passageway 28 and the opening 16 without any protrusions interrupting these spaces. Materials removed from a patient are not impeded in their outflow. Alternatively, the opening in the piston can be larger than the branch passageway 28. In all cases, and in accordance with the invention, the piston 8 when in the "on" position provides a straight-through channel connecting the first portion 29 of the branch passageway 28 with the second portion 31 of the branch passageway 28 in a linear fashion. Thus, this straight-through configuration reduces any tendency of materials to clog in the passageway 28 or the opening 16 of the piston 8.

The sheath 20 can be constructed from metals, such as, but without limitation, stainless steel; thermopolymers, such as, but without limitation, polyvinylchloride ("PVC"); and/or tephlon. Generally, thermopolymer sheaths are formed by extrusion. Typically, when a metal is used to construct the sheath 20, the sheath 20 is used within a "working" sheath, but also can be used as the "working" sheath. When a thermopolymer is used to construct the sheath 20, the sheath can be used as either the "working" sheath or within the "working" sheath. The sheath 20 can be constructed from materials that are transparent and/or translucent. Also, the outer wall of the sheath 20 that defines the lumen within can be capable of conducting light from one end of the sheath 20 to the other. For example, the outer wall can be constructed from a material with a refractive index that allows light to "bounce" along and within the wall itself.

Referring to FIG. 9A, another embodiment of a sheath assembly 52 is shown in association with an endoscopic medical device 50 ("endoscope") The sheath assembly 52 releasably attaches to the endoscope 50. The endoscope 50 includes an eyepiece 56 and an endoscope sheath 54 that fits through a housing 66 and a sheath 70 of the sheath assembly 52. The endoscope 50 includes optics for viewing material at the endoscope's 50 distal tip by looking through the eyepiece 56. These optics (for example, but without limitation, a fiber optic cable) are partially contained within the endoscope sheath 54. A viewing device (for example, but without limitation, a camera) is placed at the distal tip of the endoscope sheath 54 and is in communication with the optics and the eyepiece 56.

The connection between the sheath assembly 52 and the endoscope 50 is achieved by a connector 64 that is disposed about an opening 62 in the housing 66. Protrusions on the endoscope 50 engage with grooves in the connector 64. Relative movement between the protrusions and the grooves engages the protrusions in the grooves. Relative movement in the opposite direction disengages the protrusions from the grooves.

A piston 86 is disposed within the housing 66. The piston 86 includes a cap 58. As in the embodiment described above (FIGS. 1,2,3,4A,4B,5,6,7, and 8), a branch passageway within the housing 66 extends from the opening 60 in the nozzle 88, through an opening in the piston 86 in the "on" position (but the branch passageway is blocked in the "off" position) until it intersects with a passageway running between the sheath 70 and the opening 62. The piston 86, the seals disposed about the piston 86, the opening in the piston 86, and the passageways operate in the manner described for the previous embodiment. Additionally, a port 68 is included in the housing 66 that communicates with the passageway running between the sheath 70 and the opening 62. Alternatively, the port 68 may communicate with a channel, and not the passageway, with the channel extending through the housing 66 and down the sheath 70. The port 68 can be used to, for example, but without limitation, provide irrigating fluid to the sheath assembly 52. This irrigating fluid can be helpful during a medical procedure because it can keep the area at the tip of the sheath 70, the sheath 70 itself, and the valve clear from debris. Similarly, the irrigating fluid facilitates removal of debris by providing a medium in which debris is contained when suction is applied through the device.

One example of components that can be included within the sheath 70 is shown in FIG. 9B. The sheath 70 has an outer diameter of, for example, but not limited to, 8.4 mm, and an outer wall 72 with a thickness of, for example, but not limited to, 0.5 mm. Contained within the outer wall 72, three channels 80, 82, 84 of the endoscopic sheath 54 are shown. These channels 80, 82, 84 contain various components such as a light (and light cable) or a camera (and camera cable). Also contained within the sheath 70 can be, for example, but with out limitation, a lithotriptor 78 (e.g., 1.8 mm diameter), a 4.8 mm diameter stone 74 (without the lithotriptor 78), and/or a 3.6 mm diameter stone 76 (with the lithotriptor 78). Of course, the preceding measurements are only illustrative, and those of ordinary skill will appreciate that a range of thicknesses and diameters could be used depending upon the patient and the procedure. For example, but without limitation, sheaths of about 8 french to about 30 french are useful, however smaller or larger sizes are contemplated due to the changing size of medical devices contained within the sheath.

In operation, a medical professional positions the sheath 70 (if it is being used as a "working" sheath) within a patient at a site proximate materials of interest, such as a stone to be removed, generally as described above, and inserts the endoscope 50 through the sheath assembly 52. Alternatively, if the sheath 70 is being inserted into another "working" sheath, typically, the endoscope 50 is attached to the sheath assembly 52 and this assembled unit is inserted through the "working" sheath. By looking through the eyepiece 56, the medical professional visualizes the tissue at the distal tip of the sheath 70. The medical professional can use a lithotriptor to fragment the stone or directly suction the stone from the patient by operating the sheath assembly 52 in the manner described above (ire., turning the valve "on" to provide suction to the sheath 70). Additionally, irrigation fluid can be provided to the sheath assembly 52 via the port 68 to assist with a stone removal procedure.

Figures 10A, 10B:
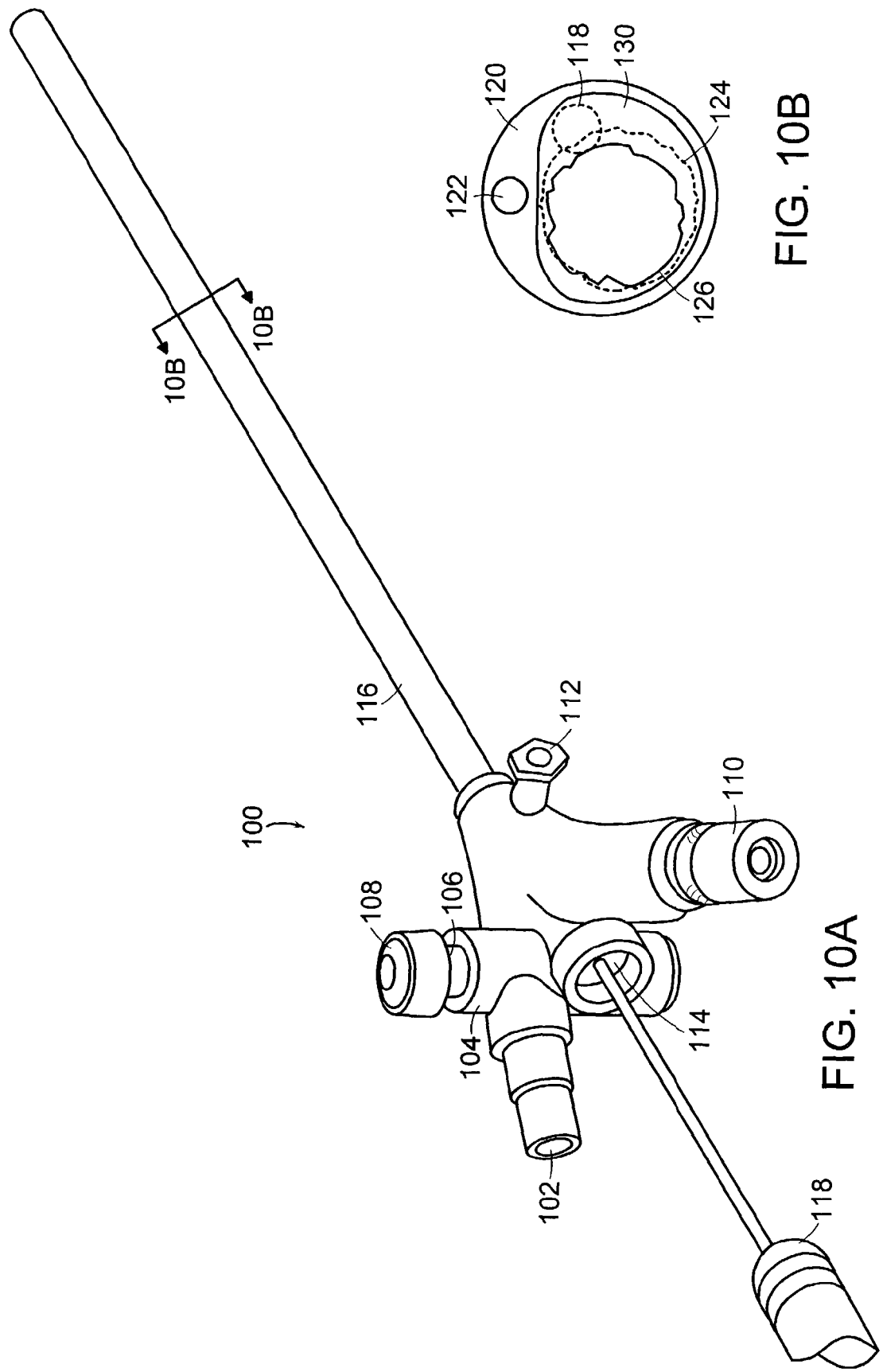
FIG. 10A shows yet another embodiment of a sheath assembly according to the invention.
FIG. 10B is a view in cross-section of the sheath portion of the assembly of FIG. 10A, taken along line 10B-10B of FIG. 10A.

Referring to FIG. 10A, another embodiment of a sheath assembly 100 has two ports 110, 112. A piston 106, that includes a cap 108 fits within a housing 104. Opening 102 attaches to tubing and/or a suction producing device (e.g., but without limitation, a vacuum). The valve and passageways of this embodiment operate in the same manner as described for the embodiments above (FIGS. 1,2,3,4A,4B, 5,6,7,8,9A, and 9B). A seal 114 is located at one end of a passageway in the housing 104 that extends to a sheath 116. The seal 114 seals around the lithotriptor 118. A lithotriptor 118, for example, can be inserted through the seal 114, down the passageway, and through the sheath 116. The sheath has an outer diameter of, for example, but s not limited to, 8.4 mm. A port 110 communicates with the passageway and is suitable for inputting, for example, but without limitation, a light and/or an endoscope. The endoscope and the optics within it can be flexible. Another port 112 communicates with the passageway and is suitable for providing an irrigating fluid down the passageway and through the sheath 70. Alternatively, the port 112 may communicate with a channel, and not the passageway, with the channel extending through the housing 66 and down the sheath 70.

One example of components that can be included within sheath 116 is shown in FIG. 10B. For example, but without limitation, a 0.5 mm thick outer wall 120 of the sheath defines two channels 122, 130. The outer wall 120, in this embodiment, also forms an internal divider between the two channels 122, 130 that is integral with the outer wall 120. In other embodiments of the invention, an internal divider can be more distinct from the outer wall. Channel 122, typically, contains a light and/or endoscope. In this embodiment, the channel is 1.2 mm in diameter. Channel 130 can contain, for example, but without limitation, a lithotriptor 118 (e.g., 1.6 mm diameter) and/or other medical devices, a 6.0 mm diameter stone 124 (without the lithotriptor 118) and/or a 5.0 mm diameter stone 126 (with the lithotriptor 118). Of course, the preceding measurements are only illustrative, and those of ordinary skill will appreciate that a range of thicknesses and diameters could be used depending upon the patient or the procedures. For example, but without limitation, sheaths of about 8 french to about 30 french are useful, however, smaller or larger sizes are contemplated due to the changing sizes of medical devices contained within the sheath. The medical devices and sheath assembly 100 are used in a manner similar to that described above (for example, but without limitation, the embodiment of FIGS. 9A and 9B) except that a smaller type of endoscope is typically employed with embodiments having a port as the point of entry for the endoscope.

Figures 11A, 11B:
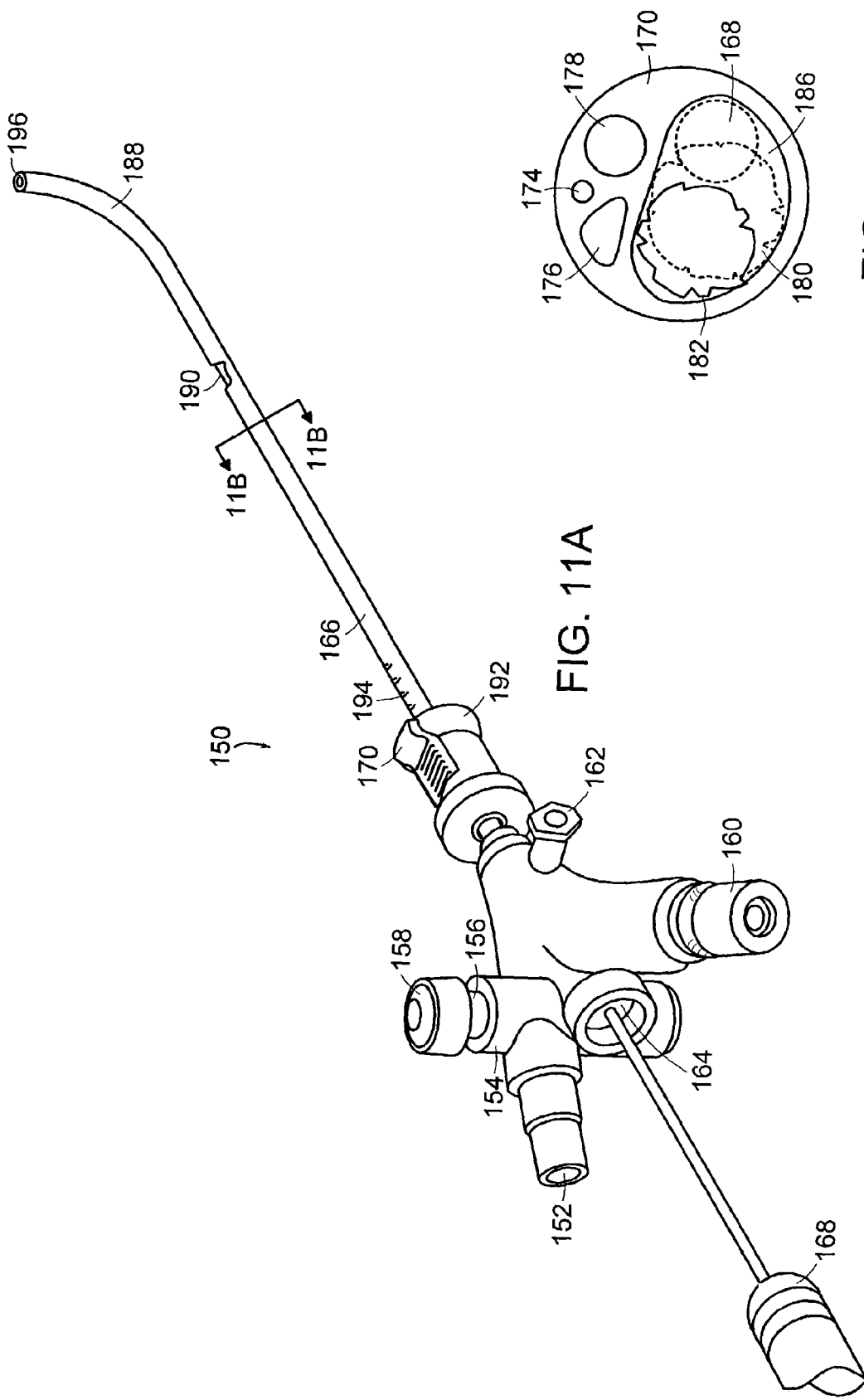
FIG. 11A shows still another embodiment of a sheath assembly according to the invention, this embodiment including a deflectable and movable sheath.
FIG. 11B is a view in cross-section of the deflectable sheath of the assembly of FIG. 11A, taken along line 11B-11B of FIG. 11A.

Referring to FIG. 11A, a sheath assembly 150 has two ports 160, 162 and a flexible sheath 166. A piston 156 with a cap 158 fits within a housing 154. Opening 152 attaches to tubing and/or a suction producing device. The valve and the passageways of this embodiment operate in the same manner as described for the embodiments above (FIGS. 1,2,3, 4A,4B,5,6, 7,8,9A,9B,10A and 10B). A seal 164 is located at one end of a passageway in the housing 154 that extends to a sheath 166. A lithotriptor 168, for example, can be inserted through the seal 164, down the passageway, and through the sheath 166. The sheath has an outer diameter of, for example, but not limited to, 5.0 mm. The sheath 166 can be deflected or moved and is shown with a bent portion 188.

The bent portion 188 is illustrative only. The sheath 166 can be positioned into any of a variety of positions. Typically, a pull wire 190 is used to produce a controllable curvature of the sheath 166.

In this embodiment, a digit-operable mechanism 192 allows a medical professional to adjust the bend in the sheath 166. A locking mechanism 170 retains the bend in the sheath 166. The pull wire 190 is attached to the distal tip 196 of the sheath 166 and to the mechanism 192. In operation, a medical professional slides the mechanism along (or produces relative movement with) the sheath 166. As the mechanism 192 moves away from the distal tip 196 a deflecture of the sheath 166 is produced. If the mechanism 192 is moved forward, the distal tip 196, the curvature of the sheath 166 is reduced. The locking mechanism 192 can be engaged with a detent 194 (only one is labeled, for clarity) to prevent the mechanism 192 from sliding along the sheath 166 and to hold the curvature of the sheath 166 in a desired position.

A port 160 communicates with the passageway and is suitable for inputting, for example, but without limitation, a light and/or an endoscope. The endoscope, optics contained within the endoscope, and/or other optics as well as the light and its cable can be flexible. Another port 162 communicates with a channel, and not the passageway, with the channel extending through the housing 154 and down the sheath. This port 162 is suitable for providing an irrigating fluid to the sheath 166. Alternatively, the port 162 may communicate with the passageway and the sheath 166.

This flexible sheath 166 allows a medical professional to perform endoscopic procedures, such as, but without limitation, PCNL with greater ease and more accuracy than with current devices. Not only does this embodiment, for example, but without limitation, reduce the likelihood of clogging during use, allow greater precision in the timing of suction application to prevent stone migration, and optionally replace a "working" sheath, but, also, allows a medical professional to selectively move the tip of the sheath to visualize a wider area within the patient as well as have access to a larger area within the patient for performing surgical procedures from a single point of entry into the patient.

In the embodiment shown in FIG. 11B, the sheath 166 has an outer wall 172 that defines four channels 174, 176, 178, 186. The outer wall 172 functions as and is integral with an internal divider, dividing the space within the sheath 166 into the four channels 174, 176, 178, 186. Channel 174 contains a 0.4 mm diameter pull wire 190 for producing curvature of the sheath 166; channel 176 can be used to transport irrigation fluids through the sheath 166; and channel 178 can contain a 1.2 mm light and/or endoscope. Any of these channels can be used for more than one purpose simultaneously. For example, one channel could contain both the light and/or endoscope and irrigation fluid simultaneously. Channel 186, the largest of the channels, can contain the lithotriptor 168 (e.g., 1.6 mm diameter) and/or other medical devices, a 2.3 mm diameter stone 182 (with the lithotriptor 168), and/or a 2.8 mm diameter stone 180 (without the lithotriptor 168). The preceding measurements are illustrative and not meant to be limiting. For example, but without limitation, sheaths of about 8 french to about 30 french are useful, however, smaller of larger sizes are contemplated due to the changing sizes of medical devices contained within the sheath. The medical devices and sheath assembly 150 would be used in a manner similar to that described above (for example, but without limitation, the embodiments of FIGS. 9A,9B,10A, and 10B).

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A sheath assembly for use with an endoscopic medical device, comprising:
   a valve assembly comprising:
     a housing defining:
       an aperture,
       a passageway that extends substantially linearly from a first opening to a second opening that opposes the first opening, and
       a branch passage extending from the aperture and being in fluid communication and intersecting with the passageway at a location between the first and second openings and at an angle greater than 90 degrees with respect to the passageway;
     a component defining an opening therethrough and disposed at least partially within the branch passage, the component interrupting the branch passage such that the branch passage includes at least two sections, the opening of the component and the at least two sections forming a substantially straight-through and continuous pathway and allowing communication between the aperture and the pathway; and
     a seal around the component; and
   a flexible sheath extending from the passageway and for passing over at least a portion of the endoscopic medical device.

2. The sheath assembly of claim 1 wherein the component is movable from an open position to a closed position to open and close the branch passageway.

3. The sheath assembly of claim 1, wherein the housing comprises a connector to allow coupling of the endoscopic medical device to the second opening.

4. The sheath assembly of claim 1 wherein the sheath is translucent or transparent.

5. The sheath assembly of claim 1 wherein the sheath comprises an outer wall defining a channel through the sheath for receiving at least a portion of the endoscopic medical device, the outer wall capable of conducting light.

6. The sheath assembly of claim 1, further comprising a pull wire for producing a curvature of the flexible sheath when actuated.

7. The sheath assembly of claim 1, wherein the sheath includes at least one internal divider defining at least two channels within the sheath.

8. The sheath assembly of claim 1 wherein the sheath further includes at least one internal divider defining at least two channels within the sheath.

9. The sheath assembly of claim 8 further comprising a pull wire for producing a curvature of the sheath when actuated.

10. The sheath assembly of claim 9 wherein the pull wire extends through at least one of the channels.

11. The sheath assembly of claim 1 wherein the sheath defines an irrigation channel.

12. A medical assembly, comprising:
    a valve housing for use in a medical procedure, the valve housing having a first, substantially linear, passageway in communication with at least first and second opposing openings in the housing, the housing also having a second passageway that is in fluid communication with and intersects the first passageway at a location between the first and second openings and at an oblique angle with respect to the first, substantially linear passageway, the second passageway being in communication with a third opening in the housing, the valve housing also including a user operated component for opening and closing the second passageway, the user operated component being located at least partially within the second passageway and being configured to close the second passageway when the component is located at a first position, the component defining an opening that forms part of a pathway from the first opening to the third opening when the component is at a second position, the component being biased toward the first position, the component including a piston; and a sheath extending from the first opening, the sheath being in communication with the first passageway and having at least one internal divider defining at least two channels within the sheath.

13. The medical assembly of claim 12, wherein the housing includes at least one port in communication with the first passageway.

14. The medical assembly of claim 12, wherein the valve housing includes a connector configured for coupling of an endoscopic medical device to the second opening.

15. The medical assembly of claim 12, wherein the sheath is translucent or transparent.

16. The medical assembly of claim 12, further comprising a pull wire for producing a curvature of the sheath.

17. The medical assembly of claim 12, wherein the sheath defines an irrigation channel.

18. A medical assembly, comprising:

valve housing for use in a medical procedure, the valve housing having a first, substantially linear, passageway in communication with at least first and second opposing openings in the housing, the housing also having a second passageway that is in fluid communication with and intersects the first passageway at an oblique angle with respect to the first, substantially linear passageway, the second passageway being in communication with a third opening in the housing, the valve housing also including user actuated means for opening and closing the second passageway at a location at least partially within the second passageway, the user actuated means defining an opening that forms part of a substantially linear pathway from the first opening to the third opening when the second passageway is opened by the user actuated means; and a flexible sheath extending from the first opening in and being in communication with the first passageway.

19. The medical assembly of claim 18, wherein the sheath is translucent or transparent.

20. The medical assembly of claim 18, further comprising a pull wire for producing a curvature of the sheath.

21. The medical assembly of claim 18, wherein the sheath includes at least one internal divider defining at least two channels within the sheath.

22. The medical assembly of claim 18, wherein the sheath defines an irrigation channel.

23. The medical assembly of claim 18, further comprising means for coupling an elongated medical device to the second opening of the valve housing such that the housing receives the elongated medical device.

24. The medical assembly of claim 18, wherein the elongated medical device includes an endoscope.

* * * * *